(12) United States Patent
Koike et al.

(10) Patent No.: US 7,056,949 B2
(45) Date of Patent: Jun. 6, 2006

(54) OIL/FAT COMPOSITION

(75) Inventors: Shin Koike, Tokyo (JP); Takeshi Yasumasu, Tokyo (JP); Tadashi Hase, Tochigi (JP); Takatoshi Murase, Tochigi (JP)

(73) Assignee: Kao Corporation, Tokyo (JP)

( * ) Notice: Subject to any disclaimer, the term of this patent is extended or adjusted under 35 U.S.C. 154(b) by 407 days.

(21) Appl. No.: 10/343,742

(22) PCT Filed: Aug. 7, 2001

(86) PCT No.: PCT/JP01/06779

§ 371 (c)(1),
(2), (4) Date: Feb. 6, 2003

(87) PCT Pub. No.: WO02/11551

PCT Pub. Date: Feb. 14, 2002

(65) Prior Publication Data

US 2004/0062847 A1   Apr. 1, 2004

(30) Foreign Application Priority Data

Aug. 8, 2000  (JP) .............................. 2000-239574

(51) Int. Cl.
*A61K 31/22* (2006.01)
*A61K 31/20* (2006.01)
*C11B 5/00* (2006.01)
*A23D 7/00* (2006.01)
*A23D 9/013* (2006.01)

(52) U.S. Cl. ..................... 514/549; 514/560; 426/541; 426/601; 426/607; 426/610

(58) Field of Classification Search ................ 514/549, 514/560; 426/541, 601, 607, 610
See application file for complete search history.

(56) References Cited

U.S. PATENT DOCUMENTS

| | | | |
|---|---|---|---|
| 5,234,699 A | 8/1993 | Yeo | |
| 5,288,619 A | 2/1994 | Brown et al. | |
| 5,308,832 A * | 5/1994 | Garleb et al. | .................. 514/2 |
| 5,935,828 A | 8/1999 | Zaks et al. | |
| 6,063,762 A * | 5/2000 | Hong et al. | .................. 514/11 |
| 6,448,292 B1 | 9/2002 | Koike et al. | |
| 6,495,536 B1 | 12/2002 | Masui et al. | |
| 2002/0002154 A1* | 1/2002 | Guivarc'h et al. | .......... 514/174 |

FOREIGN PATENT DOCUMENTS

| | | |
|---|---|---|
| EP | 0 300 844 | 1/1989 |
| EP | 0 948 902 | 10/1999 |

OTHER PUBLICATIONS

The Merck Index, 11th Edition, published 1989 by Merck & Co., Inc., p. 867, cit. 5383.*

M.F. McCarty: "Interleukin-6 as a central mediator of cardiovascular risk associted with chronic inflammation, smoking, diabetes, and visceral obesity: down-regulation with essential fatty acids, ehtanol and pentoxifylline" Database Biosis 'Online! Biosciences Information Service, May 1999 Database accession No. PREV199900353595.

Toshiyuki Shibata et al.: "Unsaturated fatty acid feeding prevents the development of acute hepatitis in Long-Evans cinnamon (LEC) rats" Database Biosis 'Online! Biosciences Information Service, Nov. 1999 Database accession No. PREV200000139637.

* cited by examiner

*Primary Examiner*—Raymond J. Henley, III
(74) *Attorney, Agent, or Firm*—Oblon, Spivak, McClelland, Maier & Neustadt, P.C.

(57) ABSTRACT

An oil/fat composition comprising 5 to 99.9 wt. % of a monoglyccride having, as fatty acid constituents thereof, 15 to 90 wt % of an ω 3-unsaturated fatty acid having less than 20 carbon atoms, 1 to 80 wt. % of an ω 9-unsaturated fatty acid and 2 to 50 wt. % of an ω 9-unsaturated fatty acid; and 0.1 to 49.9 wt. % of a diglyceride, wherein a weight ratio of the diglyceride to the monoglyceride is less than 1 and the content of a polyunsaturated fatty acid having at least 4 carbon-to-carbon double bonds is 20% or less in all the fatty acid constituents. The oil/fat composition according to the present invention has excellent processing properties, good taste and excellent lowering action against glutamic oxaloacetic transaminase (GOT) and glutamic pyruvic transaminase (GPT) levels in blood. It is useful not only for pharmaceuticals but also for preventive or remedial foods of feeds effective for hepatic function disturbances or obesity.

17 Claims, No Drawings

OIL/FAT COMPOSITION

TECHNICAL FIELD

The present invention relates to an oil/fat composition having a specific glyceride composition, a specific fatty acid composition, excellent processing properties, and characterized by the ability to lower glutamic oxaloacetic transaminase (GOT) and/or glutamic pyruvic transaminase (GPT) levels in blood. The present composition is also characterized by good body-fat burning activity.

BACKGROUND ART

Oil or fat lipids possess high caloric contents (9 kcal/g) and thereby food intake containing high quantities of these lipids can promote obesity and other life-style related diseases.

Research so far has been mainly directed to the study of fatty acids constituting a triglyceride, a principal component of a lipid. Nutritionally essential fatty acids are, for example, linoleic acid, arachidonic acid and linolenic acid. These fatty acids are known to be utilized in the body as a constituent of a biomembrane or a raw material of eicosanoids (prostaglandin, thromboxanes, leukotrienes, etc.). In addition, it is reported that there is a high possibility that a diet high in saturated fatty acids can lead to increases in the blood-serum cholesterol level, leading to atherosclerosis or heart disease (Lancet, 2, 959(1950)); and that high levels of linoleic acid oil in the diet increases tumor incidence and size in experimental animals (J. National Cancer Institute, 66, 517(1971)). It is reported that an oleic-acid-rich and saturated-fatty-acid poor diet will lower LDL-cholesterol levels, while maintaining HDL-cholesterol levels, thereby reducing the risk of heart diseases (J. Lipid Res., 26, 194(1985), New England J. Medicine, 314, 745(1988)). In addition, the physiological activity of various ω 3-unsaturated fatty acids, including antithrombus effects of eicosapentaenoic acid, contained in fish oil has drawn attention (Ann. Rev. Nutr., 8, 517(1988)). However, owing to the high degree of unsaturation of eicosapentaenoic acid and docosahexaenoic acid, these compounds have reduced stability to oxidation; and eicosapentaenoic acid is a known anticoagulant. Based on a study of the intake balance of these fatty acids, research reports recommend a ratio of saturated fatty acids: mono-unsaturated fatty acid polyunsaturated fatty acid or a ratio of ω 6-unsaturated fatty acid: ω 3-unsaturated fatty acid. Research in this area is still in progress ("Nutrition and Diseases of Oils and Fats", published by Saiwai Shobo, "The 6th edition of Recommended Dietary Allowances for Japanese, Ministry of Health and Welfare").

With a view to preventing obesity, substitutes for fats and oils or non-absorptive fats and oils have been developed and typical ones include sucrose fatty acid polyester (U.S. Pat. No. 3,600,186) which can be excreted without being absorbed into the body so that the calories derived from such a fat is essentially 0 kcal/g. There is, however, the potential problem that these fats can result in anal leakage and also may inhibit absorption of fat-soluble vitamins. Moreover, these fats do not have food value as an essential fatty acid. Nevertheless, the use of these fats have been authorized by the FDA in 1996, with the restriction that semi-solid or solid sucrose fatty acid polyesters, having a melting point of 37.8 to 71.1° C. and containing predetermined amounts of vitamins A, D, E and K, may be used only for salty snack foods.

It is also known that medium-chain fatty acid triglycerides (MCT) are not accumulated in the body, but possess poor heat stability. Similar effects have been disclosed for conjugated linoleic acid, fish oil or perilla oil (Lipids, 32, 853(1997), J. Agric. Food Chem., 46, 1225(1998)).

One recent study reported an agent containing a glyceride structure for lowering the triglyceride concentration in serum (Japanese Patent Application Laid-Open No. 5-310567), but this study focused only on the structure of monoglycerides and did not report effects of monoglycerides at maximum concentrations.

The use of polyunsaturated-fatty-acid-containing oil/fat powders (Japanese Patent Application Laid-Open No. 6-172782), polyunsaturated-fatty-acid-containing oil/fat compositions and polyunsaturated-fatty-acid-containing aqueous foods (Japanese Patent Application Laid-Open No. 7-39302), have been disclosed wherein their dispersibility in water is improved by adoption of a polyunsaturated fatty acid having a monoglyceride structure. These reports, however, only refer generally to physiological effects. One fish-oil-monoglyceride used in the above-described composition has a very unfavorable taste, is apt to become solid on storage, has a rough mouth feel, must be dissolved by heat for use and is low in linoleic acid, one of the essential fatty acids.

Accordingly, the object of the present invention is to provide an extremely useful oil/fat composition which has excellent processing properties, is safe, pleasant tasting, has hepatic function improving action, body-fat burning action, and is healthy.

DISCLOSURE OF THE INVENTION

It has now been found that an oil/fat composition using, in combination, a monoglyceride having specified fatty acid constituents and a diglyceride has excellent processing properties, is capable of lowering GOT and/or GPT levels in the blood, and has a favorable body-fat burning activity.

According to the present invention, an oil/fat composition comprising 5 to 99.9 wt. % of a monoglyceride having, as fatty acid constituents thereof, 15 to 90% of an ω 3-unsaturated fatty acid having less than 20 carbon atoms, 1 to 80% of an ω 9-unsaturated fatty acid, and 2 to 50% of an ω 6-unsaturated fatty acid, and 0.1 to 49.9% of a diglyceride, wherein a weight ratio of the diglyceride to the monoglyceride is less than 1 and the content of a polyunsaturated fatty acid having at least 4 carbon-to-carbon double bonds is 20% or less of all the fatty acid constituents. All %'s are given here as weight %'s. Throughout this specification, where ranges are provided for the components all values and sub-ranges between stated numbers are also included.

DETAILED DESCRIPTION OF THE INVENTION

The monoglyceride used in the present invention is required to have, as a fatty acid constituent, 15 to 90%, preferably 20 to 80%, more preferably 30 to 70%, especially preferably 40 to 65% of an ω 3-unsaturated fatty acid having less than 20 carbon atoms. The term "ω 3-unsaturated fatty acid" as used herein means an unsaturated fatty acid having a first unsaturated bond at the third carbon atom from the ω-position and having at least two carbon-to-carbon unsaturated bonds. Specific examples include α-linolenic acid (C18:3, all cis-9,12,15-octadecatrienoic acid) and stearidonic acid (C18:4, all cis-6,9,12,15-octadecatetraenoic acid), with α-linolenic acid being particularly preferred.

The monoglyceride further has, as a fatty acid constituent, 1 to 80%, preferably 5 to 60%, more preferably 10 to 50%, especially preferably 12 to 30% of an ω 9-unsaturated fatty acid. The ω 9-unsaturated fatty acid is a $C_{8-24}$ one, preferably a $C_{16-22}$ one. Specific examples include oleic acid, eicosamonoenoic acid and docosamonoenoic acid, with oleic acid being particularly preferred.

From the viewpoint of intake balance of fatty acids and physiologically active effects of the ω 3-unsaturated fatted acid, the monoglyceride is preferred to have, as a remaining fatty acid constituent, 2 to 50%, preferably 5 to 40%, more preferably 10 to 30% of an ω 6-unsaturated fatty acid having 18 to 22 carbon atoms such as linoleic acid and γ-linolenic acid. Of these, linoleic acid is particularly preferred. Unsaturated fatty acids are preferably contained in an amount of 70 to 100%, preferably 80 to 100%, especially 90 to 100%. Moreover, from the viewpoint of stability against oxidation and physiologically active effects, a weight ratio of the content of a fatty acid having at least two carbon-carbon double bonds to the content of (ω 9-unsaturated fatty acid+ saturated fatty acid) falls within a range of from 0.7 to 7.5, preferably from 1 to 6, more preferably from 1.2 to 5, especially from 1.5 to 4.

The oil/fat composition of the present invention contains the monoglyceride in an amount of 5 to 99.9%, preferably 40 to 99.9%, more preferably 60 to 99.5%, especially 75 to 99%. The fatty acid constituents are preferably contained in amounts of 15 to 90% of α-linolenic acid, 1 to 80% of oleic acid and 2 to 50% of linoleic acid.

The diglyceride to be used in the present invention is preferred to have fatty acid constituents similar to those of the monoglyceride.

In the oil/fat composition of the present invention, the diglyceride is present in an amount of 0.1 to 49.9%. It is added preferably in an amount of 0.1 to 25%, more preferably 0.5 to 10%, especially preferably 1 to 5% in order to have taste masking effects and to allow the monoglyceride to exhibit its maximum effect. Moreover, the diglyceride and monoglyceride are preferably incorporated at a weight ratio less than 1, preferably 0.01 to 0.8.

The oil/fat composition of the present invention may contain a triglyceride and a free fatty acid.

The triglyceride is added, as a balancing component for the oil/fat composition, in an amount not greater than 94.9%, preferably not greater than 59.9%, more preferably not greater than 39.5%, especially preferably not greater than 24% based on the oil composition, in order to have taste masking effects and allow the monoglyceride to exhibit its maximum effect.

The triglyceride has, as a fatty acid constituent, 40% or less, preferably 25% or less, especially preferably 20% or less of an ω 3-unsaturated fatty acid from the viewpoint of stability against oxidation. It contains an unsaturated fatty acid in an amount of 55 to 100%, preferably 70 to 100%, more preferably 80 to 100%, especially preferably 90 to 100%.

In the oil/fat composition of the present invention, polyunsaturated fatty acids, such as eicosapentaenoic acid, docosahexaenoic acid and arachidonic acid, having at least four carbon-to-carbon double bonds are required to be incorporated in an amount not greater than 20% of all the fatty acid constituents from the viewpoint of stability against oxidation. Their content is preferably 10% or less, more preferably 5% or less, especially preferably 2% or less, but the composition substantially free of these polyunsaturated fatty acids is most preferred.

The above-described monoglyceride is available by any one of hydrolysis reaction of a linseed oil, perilla oil, soybean oil or rapeseed oil containing an ω 3-unsaturated acyl group or ω 6-unsaturated acyl group, ester exchange reaction of the above-exemplified oil or fat with glycerin, or esterification of a fatty acid derived from such an oil or fat with glycerin. The reaction method may be either one of chemical reaction in the presence of an alkali catalyst or biochemical reaction using an enzyme such as lipase. From the viewpoint of industrial productivity, chemical reaction using alkali catalyst is more preferred The oil/fat composition of the present invention is preferably employed after purification through degumming, acid removing, washing with water, decoloring or deodorizing from the viewpoints of heat stability and taste. It is preferred that the composition contain a free fatty acid, or salt thereof, in an amount of 3.5% or less, preferably 2.5% or less, more preferably 1.5% or less, especially preferably 1% or less, most preferably 0.5% or less. In addition, it should have a peroxide value (POV, Standard Method for Analysis of Oils, Fats and Derivatives 2.5.2.1 of Japan Oil Chemists' Society) of 10 or less, preferably 7 or less, more preferably 5 or less, especially 3 or less, most preferably 1 or less. Color, referred to in the specification as color (10R+Y), is measured by the Lovibond method (Standard Method for Analysis of Oils, Fats and Derivatives 2.2.1.1 of Japan Oil Chemists' Society, 5¼ inch glass cell is used) is preferably 35 or less, referably 30 or less, especially 25 or less.

A preferred oil/fat composition of the present invention is one having a POV of 3 or less and a color (10R+Y) of 30 or less, and comprises 60 to 99.5% of the monoglyceride, 0.5 to 10% of the diglyceride, 39.5% or less of the triglyceride and 1% or less of a free fatty acid, or salt thereof, wherein the monoglyceride has, as fatty acid constituents thereof, 30 to 70% of α-linolenic acid, 10 to 50% of oleic acid, 5 to 40% of an ω 6-unsaturated fatty acid and 80 to 100% of an unsaturated fatty acid, and a fatty acid having at least two carbon-to-carbon double bonds/ω 9-unsaturated fatty acid+ saturated fatty acid) at a weight ratio of 1.2 to 5; and the content of a polyunsaturated fatty acid having at least 4 carbon-to-carbon double bonds is 2% or less in all the fatty acid constituents.

A more preferred oil/fat composition of the present invention will have a POV of 1 or less and color (10R+Y) of 25 or less, and comprises 75 to 99% of the monoglyceride, 1 to 5% of the diglyceride, 24% or less of the triglyceride and 0.5% or less of a free fatty acid, or salt thereof, wherein the monoglyceride have, as fatty acid constituents thereof, 40 to 65% of α-linolenic acid, 12 to 30% of oleic acid, 10 to 30% of an ω 6-unsaturated fatty acid, 90 to 100% of an unsaturated fatty acid, and a fatty acid having at least two carbon-to-carbon double bonds/(ω 9-unsaturated fatty acid+ saturated fatty acid) at a weight ratio of 1.5 to 4; and the content of a polyunsaturated fatty acid having at least 4 carbon-to-carbon double bonds is 0% in all the fatty acid constituents.

The oil/fat composition of the present invention will preferably contain a phytosterol in an amount of 0.05% or greater, especially 0.3% or greater from the point of view of cholesterol lowering effects. The content of a phytosterol in the oil/fat composition will depend on its raw material oil/fat or preparation process. For example, when a commercially available fatty acid obtained by distillation is used as a raw material, the content of the phytosterol in the oil/fat composition will be lowered. In this case, it is preferred to add phytosterol to provide a content of 0.05% or greater. Although no particular limitation is imposed on the upper limit of its content, a range of 0.05% to 1.2% is preferred. It may be added in an amount of 1.2% or greater when further cholesterol reduction is intended. Examples of the phytosterol include compounds in free form such as α-sitosterol, β-sitosterol, stigmasterol, campesterol, α-sitostanol, β-sitostanol, stigmastanol, campestanol and cycloartenol; and compounds in ester form such as their fatty acid esters, ferulate esters and cinnamate esters.

The oil/fat composition of the present invention may contain an antioxidant. No limitation is imposed on the antioxidant insofar as its normal use in foods or pharmaceuticals. Combination of one or more of catechin, tocopherol, vitamin C fatty acid esters, phospholipid and natural antioxidant components is preferred, with tocopherol and catechin are particularly preferred. Examples of the vitamin C fatty acid esters include palmitate esters and stearate esters, while those of the natural antioxidant components include herbs such as rosemary and extracts from the leaves or roots of a peach. The antioxidant is preferably added to the oil/fat composition of the present invention in an amount of 0.01 to 5%, especially 0.05 to 1%.

It is preferred to add a crystallization inhibitor to the oil/fat composition of the present composition.

Examples of suitable crystallization inhibitors which may be used include polyol fatty acid esters, such as polyglycerin-condensed ricinoleate esters, polyglycerin fatty acid esters, sucrose fatty acid esters, sorbitan fatty acid esters, polyoxyethylene sorbitan fatty acid esters, and propylene glycol fatty acid esters.

As the polyol fatty acid esters, those having an HLB (calculation formula of Griffin) of 4 or less, especially polyglycerin fatty acid esters, sucrose fatty acid esters and sorbitan fatty acid esters having an HLB of 3 or less are preferred.

The crystallization inhibitor is preferably added to the oil/fat composition in an amount of 0.02 to 0.5%, especially 0.05 to 0.2%.

The oil/fat composition thus obtained has excellent physiological action, such as improved hepatic function, improved body fat, visceral fat and blood triglyceride burning properties, and are seen to lower the blood sugar level, the blood pressure level, and improve insulin resistance, lowering PAI-1 and lowering leptin. Moreover, it has excellent processing properties and taste. Since an ω 3-unsaturated acyl group exists not as a free fatty acid but as an acyl group constituting the monoglyceride, the composition is active even at low concentrations and has an immediate effect. It is also characterized by a pleasant taste and is safe. These properties make it possible to use the oil/fat composition of the present invention for foods, feeds and pharmaceuticals.

The oil/fat composition of the present invention can be used in oil/fat-containing foods. Specific examples include capsules, tablets, granules, powders, bakery foods such as breads, cakes, cookies, pies, pizza crusts and bakery mixes, oil-in-water type oil/fat-containing foods such as soups, dressings, mayonnaise, coffee whiteners, whip cream and ice cream, water-in-oil type oil/fat-containing foods such as margarine, spread and butter creams, confections, for example, chocolate, caramels, candies, snacks such as potato chips, and dessert, beverages, sauces, barbecue sauces, peanut butter, baking shortening, dough, fillings, enrobers, meat processed foods, such as ham, sausage and hamburg steak, noodles, frozen foods, retort foods, cheeses and roux. The above-exemplified oil/fat-containing food can be prepared by adding, in addition to the above-described oil/fat composition, a variety of ordinary food materials depending on the type of food. The amount of the oil/fat composition of the present invention to be added to the food varies depending on the kind of the food, but is usually 0.1 to 100%, preferably 1 to 80%, especially 2 to 80%. It is preferably added in an amount of 0.1 to 50 g, preferably 0.5 to 10 g, especially 1 to 7.5 g, interms of the oil/fat composition once or several times a day. When a food contains an oil/fat derived from its basic ingredients, the ratio of the oil/fat derived from the material to the oil/fat composition of the present invention will be preferably 95:5 to 1:99, more preferably 95:5 to 5:95, still more preferably 85:15 to 5:95, especially preferably 40:60 to 5:95.

As the above-exemplified foods, examples of oil/fat containing food snacks include those containing 1 to 30%, preferably 1 to 20% of an oil/fat, 0 to 20%, preferably 1 to 20%, especially 2 to 15% of a phytosterol, 40 to 99% of a carbohydrate, and 0 to 20%, preferably 1 to 10% of a carbonating agent. The oil/fat used here has the following constitution: POV is 10 or less, preferably 3 or less, especially preferably 1 or less; the content of a monoglyceride is 5 to 99.9%, preferably 60 to 99.50, especially preferably 75 to 99%; a weight ratio of the content of the monoglyceride to diglyceride is 1 or less; the monoglyceride has, as its fatty acid constituent, 20 to 80%, preferably 30 to 70%, especially 40 to 60% of α-linolenic acid, 10 to 50%, preferably 12 to 30% of oleic acid and 5 to 40%, preferably 10 to 30% of linoleic acid; and a content of a polyunsaturated fatty acid having at least 4 carbon-to-carbon double bonds, in all the fatty acid constituents in the oil/fat, is 20% or less. Examples of the carbohydrate usable here include sucrose, glucose, fructose, maltose, xylitol, sorbitol, erythritol and starch, those of the carbonating agent include those composed of an effervescing agent such as sodium bicarbonate and acidic agent such as tartaric acid, fumaric acid or citric acid. By using such food materials, oil/fat-containing a food snack such as a tablet, candy, caramel and gummy candy can be prepared in a conventional manner. The addition of a carbonating agent makes the food especially appetizing.

Examples of pharmaceutical uses include orally administrable agents, e.g., solid preparations such as powders, granules, capsules, pills and tablets, liquid preparations such as aqueous preparations, suspensions and emulsions, and gel preparations. These types of orally administrable agents can be prepared by adding, in addition to the oil/fat composition, excipient, disintegrator, binder, lubricant, surfactant, alcohol, water, water-soluble polymer, sweetening agent, taste corrigent and acidifier, each ordinarily employed according to the dosage form of the orally administrable agent. Examples of the orally administrable preparation include cerebral function improvers. The amount of the oil/fat composition of the present invention to be added to an orally-administrable preparation differs with its using purpose or dosage form, but it is usually added in an amount of 0.1 to 100%, preferably 1 to 80%, especially 5 to 8.0. As a dose, 0.1 to 50 g, preferably 0.5 to 10 g, especially 1 to 7.5 g, in terms of the oil/fat composition, is preferably administered once or several times a day.

Examples of feed uses include livestock feed for cows, pigs, fowl and sheep, feed for small animals such as rabbits, rats and mice, feed for fishes such as eel, porgy, yellowtail and shrimp and pet foods for dogs, cats, birds and squirrels. Although the amount of the oil/fat composition of the present invention to be added to feed differs depending on the using purpose of the feed, it is usually added in an amount of 1 to 30%, with 1 to 20% being especially preferred.

The oil/fat of the present invention is preferably administered as a component of a food composition to a patient in need of reducing glutamic oxaloacetic transaminase, reducing glutaminic pyruvic transaminase, reducing body weight, reducing visceral fat weight, or treating obesity, said administration preferably being oral.

EXAMPLES

Example 1

The following oil/fat composition was prepared.

Oil/fat Composition 1

A mixture of 300 parts by weight of perilla oil (product of Ohta Oil Mill Co., Ltd.), 120 parts by weight of glycerin and 0.04 part by weight of calcium hydroxide was reacted at 220° C. for 1 hour in a nitrogen gas atmosphere, followed by neutralization with phosphoric acid. The resulting product was degassed at 200° C. and 1.3hPa by using a thin-film evaporator. An initial distillate at 180° C. and 0.4 hPa was cut and a distillate at 200° C. and 0.07 hPa was collected. Glycerin was then removed at 175° C. and 0.1 hPa (redistilling), whereby Oil/fat composition 1 was obtained.

Oil/Fat Composition 2

Oil/fat composition 2 was obtained by mixing 70 parts by weight of oil/fat composition 1 and 30 parts by weight of rapeseed oil (product of The Nisshin Oil Mills Ltd.).

Oil/Fat Composition 3

Oil/fat composition 3 was obtained by mixing 200 parts by weight of linseed oil (product of Yoshihara Oil Mill, Ltd.), 100 parts by weight of olive oil (Wako Pure Chemical Industries, Ltd.), 120 parts by weight of glycerin and 0.04 part by weight of calcium hydroxide and reacting and treating the resulting mixture in a similar manner to oil/fat composition 1.

Oil/Fat Composition 4

To a mixture of 650 parts by weight of rapeseed fatty acid and 107 parts by weight of glycerin was added "Lipozyme IM" (Novo Nordisk Bioindustry Co., Ltd.) and esterification reaction was conducted at 40° C. and 0.07 hPa for 5 hours. The reaction mixture was subjected to molecular distillation (235° C., 0.07 hPa). The residue was collected. After washing with water, deodorization was conducted at 235° C. for 1 hour, whereby Oil/fat composition 4 was obtained.

Oil/Fat Composition 5

Under similar conditions to those employed for Oil/fat composition 4, 325 parts by weight of oleic acid (product of Sigma-Aldrich) and 107 parts by weight of glycerin were esterified for 3 hours. The reaction mixture was subjected to molecular distillation (200° C., 0.07 hPa) and the resulting distillate was collected. The distillate was fractionated by chromatography on a silica gel column while using hexane: ethyl acetate as an eluting solvent (first, 100:0, then 90:10, then 80:20 and finally 70:30). The final eluent was collected, and the solvent was then removed by evaporation, whereby Oil/fat composition 5 was obtained.

Oil/Fat Composition 6

In a similar manner to that employed for Oil/Fat Composition 5 except for the use of -linolenic acid (product of Tokyo Kasei Kogyo Co., Ltd.) instead of oleic acid, reaction and treatment were conducted, whereby Oil/fat composition 6 was obtained.

Oil/Fat Composition 7

After 300 parts by weight of "DHA 45" (product of Maruha Corporation), 120 parts by weight of glycerin and 0.9 part by weight of sodium methoxide were mixed and reacted at 100° C. for 4.5 hours under a nitrogen gas atmosphere, the reaction mixture was neutralized with phosphoric acid. The resulting product was subjected to molecular distillation (200° C., 0.07 hPa) and a distillate was collected. The distillate was then fractionated by chromatography on a silica gel column while using hexane and ethyl acetate as an eluting solvent (their ratio was similar to that employed in the preparation of Oil/fat composition 5). After each fraction was evaporated and the solvent was removed, each residue was mixed again, whereby Oil/fat composition 7 was obtained.

In Table 1, the oil/fat compositions thus prepared and analytical results of fatty acids constituting a monoglyceride are shown.

TABLE 1

| | | Oil/fat composition | | | | | | |
|---|---|---|---|---|---|---|---|---|
| | | Invention product | | | Comparative product | | | |
| | | 1 | 2 | 3 | 4 | 5 | 6 | 7 |
| Glycerides composition *1 | TG | 0.0 | 29.4 | 3.8 | 13.5 | 0.0 | 0.0 | 0.0 |
| | DG | 4.1 | 3.2 | 32.0 | 85.1 | 0.0 | 0.0 | 3.7 |
| | MG | 95.9 | 67.3 | 64.2 | 1.1 | 100.0 | 100.0 | 96.3 |
| | FFA | 0.0 | 0.1 | 0.0 | 0.3 | 0.0 | 0.0 | 0.0 |
| AV | | ≦0.1 | ≦0.22 | ≦0.1 | ≦0.62 | ≦0.1 | ≦0.1 | ≦0.1 |
| POV | | 0.3 | 0.24 | 0.38 | 0.19 | ≦0.1 | ≦0.1 | 1.06 |
| Color (10 R + Y) | | 24.5 | 21.8 | 26.6 | 13.7 | 8.7 | 12.1 | 33.5 |
| MG-constituting fatty acids *2 | C18:3 3 | 58.9 | 58.8 | 40.5 | 10.5 | 0.0 | 78.2 | 0.0 |
| | C20:5 | 0.0 | 0.0 | 0.0 | 0.0 | 0.0 | 0.0 | 6.7 |
| | C22:6 | 0.0 | 0.0 | 0.0 | 0.0 | 0.0 | 0.0 | 46.3 |
| | C16:1 | 0.0 | 0.0 | 0.2 | 0.0 | 0.0 | 0.0 | 0.0 |
| | C18:1 9 | 12.8 | 13.1 | 34.3 | 57.0 | 99.1 | 0.7 | 10.5 |
| | C20:1 | 0.0 | 0.0 | 0.0 | 1.7 | 0.0 | 0.0 | 1.4 |
| | C22:1 | 0.0 | 0.0 | 0.0 | 1.0 | 0.0 | 0.0 | 1.1 |
| | C18:2 6 | 16.4 | 16.5 | 14.0 | 21.9 | 0.0 | 19.5 | 1.3 |
| | C16:0 | 5.6 | 5.6 | 7.7 | 3.7 | 0.0 | 0.0 | 11.3 |
| | C18:0 | 1.5 | 1.5 | 3.0 | 1.8 | 0.0 | 0.0 | 2.7 |
| | A ratio having at least two double bonds *3 | 3.8 | 3.7 | 1.2 | 0.5 | 0.0 | 139.6 | 2.0 |

*1: after trimethylsilylation, measured by gas chromatography
*2: after methylation, measured by gas chromatography
*3: a weight ratio of the content of a fatty acid having at least 2 carbon-to-carbon double bonds/the content of( 9-unsaturated fatty acid + saturated fatty acid)

Example 2

C57BL/6J male mice aged 7 weeks (a model of dietary type II diabetes) were divided into 6 groups, each group consisting of 5 mice and fed with the below-described diet for 4 weeks. After the rats were fasted for 18 hours, the blood was collected from the aorta abdominalis under anesthesia with ether. GOT activity and GPT activity of the serum separated from the blood were measured using asparaginic acid and alanine as substrates, respectively, in accordance with the Karmen method (J. Clin. Invest. 34, 131, 1955). The values relative to those of the control diet set at 100 are shown in Table 2.

| Diet composition: | | |
|---|---|---|
| | Control diet | Test diet |
| Casein | 20.0% | 20.0% |
| Soybean oil | 20.0 | 20.0 |
| Lard | 10.0 | 10.0 |
| Oil/fat composition | 0.0 | 4.0 |
| Mineral mixture | 3.5 | 3.5 |
| Vitamin mixture | 1.0 | 1.0 |
| Cellulose | 4.0 | 4.0 |
| Sucrose | 13.0 | 13.0 |
| Starch | 28.5 | 24.5 |

TABLE 2

| Oil/fat composition | | GOT activity | GPT activity | Weight gain | Visceral fat weight |
|---|---|---|---|---|---|
| Invention Products | 1 | 81.6* | 55.4* | 67.3* | 56.2* |
| | 2 | 85.1* | 77.3* | — | — |
| | 3 | 86.9 | 79.2* | — | — |
| Comparative Products | (Control diet) | 100 | 100 | 100 | 100 |
| | Perilla oil | 121 | 113 | 122* | 117* |
| | 5 | 110 | 108 | — | — |

Test on significant difference from control diet group
(Student t-test)
*p < 0.05
**p < 0.01

Visceral fat weight; total of perinephric, mesenteric, retroperitoneal and epididymal fat weights.

The oil/fat compositions according to the present invention each exhibited excellent effects for lowering GOT and GPT levels in blood and reducing a body weight and a visceral fat weight.

Example 3

The results of hydration property and standing stability of the oil/fat composition are shown in Table 3.

Test on hydration property: By a disperser, 1 part by weight of an oil/fat composition and 99 parts by weight of water were stirred (for 5 minutes at 10000 r/min). The reaction mixture was allowed to stand at 5° C. for 24 hours and the condition was visually observed based on the following standards.

Evaluation Surface Condition
A: No floating of an oil is observed on the surface.
B: Slight floating of an oil is observed on a part of the surface.
C: Floating of an oil is observed
D: The mixture is turbid and existence of an oil layer is recognized.

Test on static stability: An oil/fat composition was allowed to stand at 35° C. for 24 hours and the condition of the composition was visually observed based on the following standards:

Evaluation Condition
A: The composition is transparent.
B: A slight turbidity is recognized.
C: The composition is turbid but has fluidity.
D: The composition is turbid and lacks fluidity.

| Oil/fat composition | Hydration property | Static stability |
|---|---|---|
| Invention product | | |
| 1 | A | A |
| 2 | B | A |
| 3 | B | A |
| Comparative product | | |
| 4 | C | A |
| 7 | A | D |
| Perilla oil | C | A |

The invention products were transparent when allowed to stand at 35° C. so that it has good workability, melts well in the mouth, has good hydration property and has excellent processing properties.

Example 4

Tablets were prepared as follows. An oil/fat composition was prepared by mixing 100 parts by weight of Oil/fat composition 1, 0.02 part by weight of Mix Vitamin E "MDE-6000" (product of Yashiro Co., Ltd.), 0.5 part by weight of catechin "Sunkatol No. 1" (product of Taiyo Kagaku Co., Ltd.), 0.25 part by weight of rosemary "Herbalox type HT-0 Extract" (product of Kalsec, Inc.) and 2.0 parts by weight of a phytosterol (product of Tama Biochemical Co., Ltd.). A mixture of 10 parts by weight of the resulting oil composition, 44 parts by weight of corn starch, 40 parts by weight of crystalline cellulose, 5 parts by weight of carboxymethylcellulose calcium, 0.5 part by weight of silicic anhydride and 0.5 part by weight of magnesium stearate was compressed into tablets (each, 200 mg in weight).

Example 5

Soft capsules were prepared as follows. An oil/fat composition was prepared by mixing 100 parts by weight of Oil/fat composition 1, 0.02 part by weight of "Mix Vitamin E MDE-6000" (product of Yashiro Co., Ltd.), 0.7 part by weight of catechin "Sunkatol No.1" (Taiyo Kagaku Co., Ltd.), 0.02 part by weight of Vitamin C palmitate (product of Roche, Ltd.), 0.1 part by weight of a phytosterol (product of Tama Biochemical Co., Ltd.) and 0.15 part by weight of polyglycerin fatty acid ester "THL3" (product of Sakamoto Yakuhin Kogyo Co., Ltd.). The resulting oil/fat composition (300 mg) was encapsulated in oval-shaped soft capsules, whereby soft capsules were prepared.

Example 6

Hamburg steaks were prepared as follows. The below-described food materials were mixed under stirring in a food processor and formed into oblong patties, each 80 g. After baking them on a hot plate at 230° C. for 2 minutes, they were heated in an oven at 200° C. for 7 minutes. They were wrapped individually and quick frozen at −40° C. for 40 minutes. After they were preserved at −20° C. for 1 week, they were boiled for 10 minutes and provided for tasting.

| Composition ratio of food materials: | |
| --- | --- |
| Minced meat (beef:pork = 7:3) | 65.0% |
| Onion (roasted) | 10.0 |
| Whole egg | 5.0 |
| Soybean protein | 5.0 |
| Crumbled bread | 5.0 |
| Corn starch | 2.0 |
| Salt | 1.0 |
| Nutmeg | 0.3 |
| Pepper | 0.2 |
| Water | 6.5 |
| Oil/fat composition* (Table 4) | 1.5 |

*added with 0.02 part by weight of tocopherol based on 100 parts by weight of the oil/fat composition.

Average evaluation by a panel of 10 experts based on the following standards is shown in Table 4.

| Evaluation | Taste | Juicy feel | Soft feel |
| --- | --- | --- | --- |
| A | Very delicious | Very juicy | Very soft |
| B | Delicious | Juicy | Soft |
| C | Not so delicious | Slightly dry | Slightly hard |
| D | Distasteful | Dry | Hard |

TABLE 4

| | Oil/fat composition | | | |
| --- | --- | --- | --- | --- |
| | 2 | 6 | 7 | Perilla Oil |
| Taste | A | C | D | B |
| Juicy feel | A | A | A | C |
| Soft feel | A | A | A | C |

It has been found that hamburg steaks made using Oil/fat composition 2 of the present invention were soft, juicy, rich in taste, not greasy and were utterly free from a rancid odor due to deterioration, had excellent processing properties, and were markedly delicious.

Example 7

The boiled noodles were prepared as follows. For 15 minutes, 100 parts by weight of wheat flour, 32 parts by weight of water, 2 parts by weight of salt and 0.5 part by weight of an oil/fat composition were kneaded. The kneaded mass was then allowed to stand for 30 minutes at room temperature, spread under pressure and cut into noodles. After boiling for 15 minutes in boiling water of 10 times the weight of the noodles, they were cooled with running water and drained, whereby boiled noodles were obtained. These noodles refrigerated at 10° C. for one day were boiled for 1 minute and provided for tasting.

Average evaluation of a panel of 10 experts based on the following evaluation standards is shown in Table 5.

| Evaluation | Taste | Surface luster | Separability of noodles |
| --- | --- | --- | --- |
| A | Very delicious | Very lustrous | Very good |
| B | Delicious | Lustrous | Good |
| C | Not so delicious | Not so lustrous | Not so good |
| D | Bad taste | Having no luster | Bad |

TABLE 5

| | Oil/fat composition | | |
| --- | --- | --- | --- |
| | 1 | 7 | Perilla oil |
| Taste | A | C | B |
| Surface luster | A | A | D |
| Separability of noodles | A | A | D |

It has been found that boiled noodles made using Oil/fat composition 1 of the present invention had a smooth surface, had luster, did not stick to each other and were separated easily, were rich in taste, were not greasy and were utterly free from a rancid odor due to deterioration, had excellent processing properties, and were markedly delicious.

Example 8

The tablets of candy having the following composition were prepared.

| | Parts by weight |
| --- | --- |
| Xylitol | 28.4 |
| Sorbitol | 56.9 |
| Oil/fat composition 1 | 2.5 |
| Phytosterol (product of Tama Biochemical Co., Ltd.) | 2.5 |
| Flavor (ginger oil) | 1.2 |
| Citric acid | 3.0 |
| Sodium bicarbonate | 5.0 |
| Colorant (turmeric powder) | 0.5 |

After the above-described raw materials were mixed, the mixture was ground in a mortar. The resulting grind was compressed (24.5 Mpa, 4 seconds) into tablets of candy, each 2 g in weight, in a conventional manner by a tableting machine.

INDUSTRIAL APPLICABILITY

The oil/fat composition according to the present invention has excellent processing properties, pleasant taste and excellent activity capable of lowering glutamic oxaloacetic transaminase (GOT) and glutanic pyruvic transaminase (GPT) levels in the blood. It is useful not only for pharmaceuticals but also for preventive or remedial foods or feeds effective for hepatic function disturbances or obesity.

This application is based on Japanese application, 2000-239574, filed in the Japanese Patent office on Aug. 8, 2000, the entire contents of which are hereby incorporated by reference.

The invention claimed is:

1. An oil/fat composition comprising 5 to 99.9 wt. % of a monoglyceride mixture having, as a fatty acid constituent thereof, 15 to 90 wt. % of an ω 3-unsaturated fatty acid having less than 20 carbon atoms, 1 to 80 wt. % of an ω 9-unsaturated fatty acid and 2 to 50 wt. % of an ω 6-unsaturated fatty acid; and 0.1 to 49.9% of a diglyceride, wherein the weight ratio of the diglyceride to the monoglyceride is less than 1 and a content of polyunsaturated fatty acids having at least 4 carbon-to-carbon double bonds is 20 wt. % or less of all the fatty acid constituents.

2. An oil/fat composition according to claim 1, which has a peroxide value (POV) of 10 or less and contains α-linolenic acid as the ω 3-unsaturated fatty acid.

3. An oil/fat composition according to claim 1 or 2, which has a peroxide value (POV) of 3 or less, has a color (10R+Y) of 30 or less which comprises 60 to 99.5 wt. % of the monoglyceride mixture, 0.5 to 10 wt. % of the diglyceride, and further comprises 39.5 wt. % or less of a triglyceride and a free fatty acid or salt thereof of 1 wt. % or less, wherein the monoglyceride mixture has as a fatty acid constituent thereof 30 to 70 wt. % of α-linolenic acid, 10 to 50 wt. % of oleic acid, 5 to 40 wt. % of the ω6-unsaturated fatty acid, 80 to 100 wt. % of the fatty acid constituents being unsaturated fatty acids, and a ratio of fatty acids having at least two carbon-to-carbon double bonds/(ω9-unsaturated fatty acid+ saturated fatty acid) of 1.2 to 5; wherein the content of polyunsaturated fatty acids having at least 4 carbon-to-carbon double bonds is 2 wt. % or less of all of the fatty acid constituents.

4. An oil/fat composition according to claim 1 or 2, which has a POV of 1 or less, has a color (10R+ Y) of 25 or less, comprises 75 to 99 wt. % of the monoglyceride mixture, 1 to 5 wt. % of the diglyceride, 24 wt. % or less of a triglyceride and a free fatty acid or salt thereof of 0.5 wt. % or less, wherein the monoglyceride mixture has as a fatty acid constituent thereof 40 to 65 wt. % of α-linolenic acid, 12 to 30 wt. % of oleic acid, 10 to 30 wt. % of the ω 6-unsaturated fatty acid, 90 to 100 wt. % of fatty acid constituents being unsaturated fatty acids; and a ratio of a fatty acid having at least two carbon-to-carbon double bonds/(ω 9-unsaturated fatty acid+ saturated fatty acid) of 1.5 to 4; and wherein the content of polyunsaturated fatty acids having at least 4 carbon-to-carbon double bonds is 2 wt. % of all the fatty acid constituents.

5. An oil/fat composition according to any one of claims 1 to 2, further comprising a phytosterol in an amount of 0.05 wt. % or more.

6. An oil/fat composition according to any one of claims 1 to 2, further comprising 0.02 to 0.5 wt. % of a crystallization inhibitor.

7. An oil/fat composition according to any one of any one of claims 1 to 2, further comprising 0.01 to 5 wt. % of an antioxidant.

8. A food containing an oil/fat composition as claimed in any one of claims 1 to 2.

9. A feed containing an oil/fat composition as claimed in any one of claims 1 to 2.

10. A pharmaceutical composition containing an oil/fat composition as claimed in any one of claims 1 to 2.

11. Method of preparing a food article comprising mixing one or more food materials with the oil/fat composition of as claimed in any one of claims 1 to 2.

12. A method of reducing glutamic oxaloacetic transaminase and glutamic pyruvic transaminase in the blood of a subject in need thereof comprising administering to said subject the oil/fat composition as claimed in any one of claims 1 to 2 in the form of a food composition.

13. The method as claimed in claim 12, wherein said food composition comprises said oil/fat composition in an amount of 0.1 to 100%.

14. A method of reducing body weight and visceral fat weight in an human or an animal subject in need thereof comprising administering to said subject in need thereof, a food composition comprising the oil/fat composition as claimed in any one of claims 1 to 2 in the form of a food composition.

15. The method as claimed in claim 14, wherein said food composition comprises said oil/fat composition in an amount of 1 to 80%.

16. A method of treating obesity comprising administering to a subject in need thereof, a food composition comprising the oil/fat composition as claimed in any one of claims 1 to 2.

17. The method as claimed in claim 16 wherein said food composition comprises said oil/fat composition in an amount of 2 to 80%.

* * * * *

UNITED STATES PATENT AND TRADEMARK OFFICE
CERTIFICATE OF CORRECTION

| | | |
|---|---|---|
| PATENT NO. | : 7,056,949 B2 | Page 1 of 1 |
| APPLICATION NO. | : 10/343742 | |
| DATED | : June 6, 2006 | |
| INVENTOR(S) | : Shin Koike et al. | |

It is certified that error appears in the above-identified patent and that said Letters Patent is hereby corrected as shown below:

In the Claims:

Column 14, Claim 14, lines 27-28, delete "in need thereof, a food composition comprising".

Signed and Sealed this

Third Day of October, 2006

JON W. DUDAS
*Director of the United States Patent and Trademark Office*